United States Patent
Zheng et al.

(10) Patent No.: US 10,465,039 B2
(45) Date of Patent: Nov. 5, 2019

(54) EPOXY CURING AGENTS, COMPOSITIONS AND USES THEREOF

(71) Applicant: EVONIK DEGUSSA GMBH, Essen (DE)

(72) Inventors: Shiying Zheng, Center Valley, PA (US); Sudhir Ananthachar, Hillsborough, NJ (US); Robert Rasing, Rotterdam (NL); Nergiz Bozok, Utrecht (NL); Shafiq Fazel, Allentown, PA (US); Michael Oberlander, Topton, PA (US)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/596,996

(22) Filed: May 16, 2017

(65) Prior Publication Data

US 2017/0247501 A1    Aug. 31, 2017

Related U.S. Application Data

(63) Continuation-in-part of application No. 15/343,632, filed on Nov. 4, 2016.

(60) Provisional application No. 62/256,262, filed on Nov. 17, 2015.

(51) Int. Cl.
| | | |
|---|---|---|
| *C08G 59/50* | (2006.01) | |
| *C08G 59/24* | (2006.01) | |
| *C09D 163/00* | (2006.01) | |
| *C04B 24/28* | (2006.01) | |
| *C04B 28/04* | (2006.01) | |
| *C07D 233/02* | (2006.01) | |
| *C07D 487/08* | (2006.01) | |
| *C08G 59/56* | (2006.01) | |
| *C08G 59/60* | (2006.01) | |

(52) U.S. Cl.
CPC ........ *C08G 59/5073* (2013.01); *C04B 24/281* (2013.01); *C04B 28/04* (2013.01); *C07D 233/02* (2013.01); *C07D 487/08* (2013.01); *C08G 59/245* (2013.01); *C08G 59/502* (2013.01); *C08G 59/508* (2013.01); *C08G 59/56* (2013.01); *C08G 59/60* (2013.01); *C09D 163/00* (2013.01); *C04B 2201/52* (2013.01)

(58) Field of Classification Search
None
See application file for complete search history.

(56) References Cited

U.S. PATENT DOCUMENTS

| | | |
|---|---|---|
| 2,643,977 A | 6/1953 | Hughes |
| 4,269,742 A | 5/1981 | Goeke et al. |
| 4,289,869 A | 9/1981 | Zengel et al. |
| 4,533,682 A | 8/1985 | Tortorello et al. |
| 4,877,578 A | 10/1989 | Zetlmeisl et al. |
| 6,465,601 B1 | 10/2002 | Wiesendanger et al. |
| 8,147,964 B2 | 4/2012 | Vedage et al. |
| 8,168,296 B2 | 5/2012 | Vedage et al. |
| 8,518,547 B2 | 8/2013 | Vedage et al. |
| 8,519,091 B2 | 8/2013 | Raymond |
| 9,550,912 B2 | 1/2017 | Flosser et al. |
| 2008/0255271 A1* | 10/2008 | Raymond ............... C04B 26/14 523/437 |
| 2009/0023846 A1 | 1/2009 | Vedage et al. |
| 2009/0029175 A1* | 1/2009 | Vedage ............... C08G 59/502 428/418 |
| 2009/0163676 A1 | 6/2009 | Vedage et al. |
| 2016/0177125 A1* | 6/2016 | Flosser ............... C08G 59/502 523/400 |
| 2017/0137562 A1 | 5/2017 | Zheng et al. |

FOREIGN PATENT DOCUMENTS

| | | |
|---|---|---|
| CN | 103333136 A | 10/2013 |
| DE | 2321509 A1 | 11/1973 |
| EP | 0458502 A2 | 11/1991 |
| JP | H06122754 A | 5/1994 |
| JP | 5408612 B2 | 2/2014 |
| WO | 2013003202 A1 | 1/2013 |

OTHER PUBLICATIONS

Araki Macromol. vol. 21, No. 7, 1997-2001.*
Araki et al.; Macromolecules: Site-Selective Derivatization of Oligoethylenimines Using Five-Membered-Ring Protection Method, vol. 21, No. 7, 1988, pp. 1995-2001, XP055346775 (8 pages).
van Alphen, J. et al; N.N'-Di-(Benzyl)-Ethylenediamine:(Alkylated Ethylenediamnine derivates I); vol. 54, No. 2, pp. 93-96, XP055346671 (4 pages).
Hine, J. et al; Imines, Imidazolidines, and Imidazolidinium Ions from the Reactions of Ethylenediamine Derivates with Isobutyraldehyde and Acetone; Journal of American Cancer Society; 1973, Columbus, Ohio, XP055346492 (7 pages).
Tanaka; Synthesis and Characteristics of Epoxides, C.A. May, ed; Epoxy Resins Chemistry and Technology; Marcel Dekker; 1988; (11 pages).

(Continued)

*Primary Examiner* — Robert T Butcher

(74) *Attorney, Agent, or Firm* — Andrew H. Chung; Linda S. Li; Jason S. Ngui

(57) ABSTRACT

The present invention relates to epoxy curing agents which are obtained from the reaction of a polyalkylene polyether modified polyepoxide resin and a polyamine component. They polyamine component is a reaction product of a polyethylene polyamine having 3 to 10 nitrogen atoms, for example, diethylenetriamine (DETA), and at least one aldehyde having 1 to 8 carbon atoms, for example, formaldehyde. The epoxy curing agent may be used as part of a two component coating system in the curing of liquid or pre-dispersed curable epoxy resins.

18 Claims, No Drawings

(56) References Cited

OTHER PUBLICATIONS

Huntsman; Ethyleneamines: A Global Profile of Products and Services; 2007; (76 pages).
Gajendra D. Khune and Nanasaheb G. Ghatge; Amine Aldehyde Condensation Products for Stabilization of Natural Rubber Latex Foam; Journal of Macromolecular Science; Part A—Chemistry; Pure and Applied Chemistry, col. A(15), No. 1, pp. 153-168; 1981. (16 pages).
Ukrainskii Khimicheskii Zhurnal (Russian Edition), vol. 54, Issue 4, p. 387-389, Journal, 1988. (3 pages).
H. Lee and K. Neville; Handbook of Epoxy Resins; Chapter 5: Epoxy-Resin Curing Mechanisms; McGraw Hill; New York; 1967; pp. 5-1 to 5-25 (13 pages).

\* cited by examiner

EPOXY CURING AGENTS, COMPOSITIONS AND USES THEREOF

FIELD OF THE INVENTION

The present invention relates generally to curing agents for epoxy resin, the amine-epoxy compositions derived therefrom and articles produced from such compositions. Methods for making and using the curing agents and compositions are also disclosed.

BACKGROUND OF THE INVENTION

Epoxy resin based systems are widely used as sealing materials, coating compositions, adhesives, and the like, in a variety of fields such as electricity, electronics, and civil engineering and construction. When cured, they exhibit excellent electrical insulating properties, are moisture proof, heat resistant, soldering resistant, chemical resistant, durable, have excellent adhesive properties and mechanical strength. Specific examples include epoxy composite materials using carbon fiber and fiberglass reinforcements, protective coatings for metal surfaces, and protective coatings for concrete, cementitious or ceramic substrates, often referred to as civil engineering applications.

Two part epoxy resin based systems generally include a curable epoxy resin and a curing agent for the epoxy resin. The two components chemically react with each other to form a cured epoxy, which is a hard, duroplastic material. Epoxy resins are substances or mixtures which contain epoxide groups. The curing agents include compounds which are reactive to the epoxide groups of the epoxy resins, such as amines, carboxylic acid, and mercaptanes.

During preparation, one or both of the epoxy resin and curing agent are dispersed or dissolved in a solvent, for example, an organic solvent, to reduce viscosity. Significant environmental and safety concerns are created due to the use of such solvent-based systems since the associated volatile organic compounds (VOCs) create environmental pollution and health hazards.

A variety of epoxy resin curing agents dissolved or emulsified in water have been developed to address the environmental and health concerns. For example: U.S. Pat. No. 4,197,389 discloses a curing agent prepared by reacting at least one polyepoxide compound with at least one polyalkylene polyether polyol to form an adduct which is subsequently reacted with a polyamine; U.S. Pat. No. 5,032,629 describes water compatible polyamine-epoxy adducts prepared by reacting poly(alkylene oxide) mono- or diamines with a polyepoxide to form intermediates which are then subsequently reacted with an excess of a polyamine; U.S. Pat. No. 6,245,835 describes amino-epoxy adduct curing agents prepared by reacting a polyoxyalkylenediamine with a polyepoxide and polyoxyalkylene glycol diglycidyl ether and emulsifying the reaction product in water.

Many current waterborne curing agent and epoxy systems are plagued with problems which limit their usefulness. One problem is cured coatings having poor physical properties, such as hardness, appearance and solvent resistance. Other problems are a relatively high viscosity of the curing agent, making the coatings difficult to apply. Additional problems include a slow cure speed, short pot life and manufacturing difficulties. It is an object of the present invention to provide a novel, low VOC, waterborne curing agent for use with epoxy resin compositions, which overcomes these problems. It is also an object of the present invention to provide waterborne curing agents that, can be easily manufactured, have improved pot life and exhibit low viscosity, even at high solids content.

SUMMARY OF THE INVENTION

In one aspect, the present invention provides an epoxy curing agent for a curable epoxy resin. The curing agent comprises the reaction product of a polyalkylene polyether modified polyepoxide resin component and a polyamine component which is the reaction product of a polyethylene polyamine and an aldehyde. In a preferred embodiment, the polyamine component is the reaction product of diethylenetriamine (DETA) and formaldehyde. The curing agent comprises the contact product of the curing agent described above and water.

In another aspect, the present invention provides a method for the preparation of the epoxy curing agent such that the reaction product contains active amine hydrogens capable of reacting with a curable epoxy resin.

In still another aspect, the present invention relates to the use of the above curing agent for curing a liquid or pre-dispersed epoxy resin in a two component amine-epoxy system. The amine-epoxy systems comprising the epoxy curing agent of the present invention have a fast cure rate, and a cured composition which exhibits good chemical resistance, fast hardness development, good gloss and stability. Articles of manufacture produced from amine-epoxy compositions disclosed herein include, but are not limited to, adhesives, coatings, primers, sealants, curing compounds, construction products, flooring products, and composite products.

DETAILED DESCRIPTION

The ensuing detailed description provides preferred exemplary embodiments only, and is not intended to limit the scope, applicability, or configuration of the invention. Rather, the ensuing detailed description of the preferred exemplary embodiments will provide those skilled in the art with an enabling description for implementing the preferred exemplary embodiments of the invention. Various changes may be made in the function and arrangement of elements without departing from the spirit and scope of the invention, as set forth in the appended claims.

In the claims, letters may be used to identify claimed method steps (e.g. a, b, and c). These letters are used to aid in referring to the method steps and are not intended to indicate the order in which claimed steps are performed, unless and only to the extent that such order is specifically recited in the claims.

Contact product, as used herein, describes a composition wherein the components are contacted together in any order, in any manner, and for any length of time, including the possibility that two or more of the components may react with one another forming other components. For example, the components can be contacted by blending or mixing. Further, contacting of any component can occur in the presence or absence of any other component of the compositions or formulations described herein. Combining additional materials or components can be done by any method known to one of skill in the art. Further, the term "contact product" includes mixtures, blends, solutions, dispersions, slurries, reaction products, and the like, or combinations thereof. Although "contact product" can include reaction products, it is not required for the respective components to react with one another.

Reaction product, as used herein, describes a composition wherein one or more of the components are produced as a result of a chemical reaction between two or more reactants.

As used herein, pot life in coating application refers to the time period in which a composition is sufficiently liquid such that it may be applied to a substrate material, and achieve desired quality coatings.

The phrases "in one embodiment," "according to one embodiment," and the like generally mean the particular feature, structure, or characteristic following the phrase is included in at least one embodiment of the present invention, and may be included in more than one embodiment of the present invention. Importantly, such phrases do not necessarily refer to the same embodiment.

The present invention is generally directed to epoxy curing agents and methods of making and using such epoxy curing agents. These waterborne epoxy curing agents can be used to cure, harden and/or cross-link a curable epoxy resin.

The curing agents of the present invention are simple to manufacture and deliver a fast cure speed when used to cure liquid epoxy resin and solid epoxy resin dispersions. The coating compositions prepared with the curing agents described herein have a relatively low viscosity, making them easy to apply to substrates, and an acceptable pot life. The cured coating compositions exhibit fast hardness development and good film appearance.

An aspect of the present invention is a curing agent comprising the reaction product of: (1) a polyalkylene polyether modified polyepoxide resin component, and (2) a polyamine component, which is the reaction product of (2a) a polyethylene polyamine and (2b) an aldehyde. In a preferred embodiment, the polyamine component is the reaction product of DETA and formaldehyde.

Aqueous or waterborne curing agent compositions are within the scope of the present invention. Waterborne curing agent compositions comprise the contact product of the above described curing agent and water. Such aqueous curing agent compositions preferably comprise 30 to 80 wt % solids, more preferably 50 to 70 wt % solids.

Generally, the curing agent compositions have an amine hydrogen equivalent weight (AHEW) based on 100% solids from about 30 to about 500. Further, such curing agent compositions can have an AHEW based on 100% solids in the range from about 50 to about 450, from about 50 to about 400, from about 50 to about 350, from about 50 to about 300, from about 50 to about 250, from about 50 to about 200, from about 100 to about 250, or from about 100 to about 200.

The curing agent compositions may be used as one component of a two-component amine-epoxy coating composition, wherein the second component is a curable epoxy component. The epoxy component of the two component coating composition comprises an epoxy resin or an epoxy resin dispersion.

(1) The Polyalkylene Polyether Modified Polyepoxide Resin Component of the Curing Agent The polyalkylene polyether modified polyepoxide resin may be produced by any effective method, for example, by reacting a polyepoxide compound with a polyalkylene polyether polyol, or by reacting a polyepoxide compound with a polyetheramine.

In an embodiment, the modified polyepoxide resin component is prepared via a polyalkylene polyether polyol. Polyalkylene polyether modified polyepoxide resins useful in the current invention may comprise the reaction product of: (i) at least one polyepoxide compound and (ii) at least one polyalkylene polyether polyol. Suitable polyepoxide compounds and admixtures thereof are disclosed in U.S. Pat. No. 4,197,389. The disclosure of U.S. Pat. No. 4,197,389 is incorporated herein by reference in its entirety.

The at least one polyepoxide compound includes, but is not limited to, a diglycidyl ether of bisphenol A, a diglycidyl ether of bisphenol F, an epichlorohydrin-derived compound, or a combination thereof. Generally, polyepoxide resins with epoxy equivalent weights in the range from about 160 to about 2000 are useful in the present invention. In a preferred embodiment, the at least one polyepoxide resin comprises a difunctional bisphenol A/epichlorohydrin-derived liquid epoxy resin.

Suitable polyalkylene polyether polyols are described in U.S. Pat. No. 4,197,389. Non-limiting examples of polyalkylene polyether polyols that are useful in the present invention include, but are not limited to, polyethylene glycols, polypropylene glycols, or combinations thereof. Mixtures of different molecular weight polyalkylene polyether polyols can be used, as well as mixtures of different polyalkylene polyether polyols. The combinations of the different polyether polyols can be mixed first and then reacted with the polyepoxide resin, or can be reacted separately with the polyepoxide resin and subsequently mixed or blended. Generally, polyalkylene polyether polyols with number average molecular weights in the range from about 200 to 10,000, from about 400 to about 8000, from about 600 to about 5000, or from about 800 to about 2500, are useful in the present invention.

The polyepoxide resin can be reacted with the polyalkylene polyether polyol in accordance with the process described in U.S. Pat. No. 4,197,389. Often, a Lewis acid catalyst is used to promote the reaction, such as a $BF_3$-amine complex which is a well-known catalyst to those of skill in the art. In addition, the reaction can be conducted in the presence of monoepoxides and solvents or softeners, as is known to those of skill in the art. Exemplary monoepoxides that can be used in admixture with the polyepoxide resin include, but are not limited to, epoxidized unsaturated hydrocarbons such as butylene, cyclohexene, and styrene oxides, and the like; halogen-containing epoxies such as epichlorohydrin; epoxyethers of monohydric alcohols such as methyl, ethyl, butyl, 2-ethylhexyl, dodecyl alcohol, and the like; epoxy-ethers of monohydric phenols such as phenol, cresol, and other phenols substituted in the ortho or para positions; glycidyl esters of unsaturated carboxylic acids; epoxidized esters of unsaturated alcohols or unsaturated carboxylic acids; acetals of glycidaldehyde; or combination thereof.

To produce polyalkylene polyether modified polyepoxide resins useful in the present invention, the reactant ratio of epoxy groups in the polyepoxide compound to the hydroxyl groups in the polyalkylene polyether polyol is generally within a range from about 1.5:1 to about 8:1. The reactant ratio, in accordance with another aspect of the present invention, is about 1.6:1, about 2:1, about 2.5:1, about 3:1, about 3.5:1, about 4:1, about 4.5:1, about 5:1, about 5.5:1, about 6:1, about 6.5:1, about 7:1, or about 7.5:1. In yet another aspect, the reactant ratio is in a range from about 1.8:1 to about 6:1. In a further aspect, the reactant ratio of epoxy groups in the polyepoxide compound to the hydroxyl groups in the polyalkylene polyether polyol is in a range from about 2:1 to about 4:1.

In an embodiment, the polyalkylene polyether modified polyepoxide resin component is prepared via the reaction of amino-terminated polyalkylene polyether (polyetheramine) with a polyepoxide compound. Polyalkylene polyether modified polyepoxide resins useful in the current invention comprise the reaction product of: (i) at least one polyepoxide compound and (ii) at least one polyetheramine.

Polyetheramines useful for reacting with the polyepoxide resin component include compounds which contain primary amino groups attached to the end of a polyether backbone. The polyether backbone is normally based on either propylene oxide (PO), ethylene oxide (EO), or mixed PO/EO. Preferably the polyether amine is a monoamine having an average molecular weight from about 500 to about 4000, or about 500 to about 3,000, or about 500 to about 2,000. The reaction product of a polyether amine and a polyepoxide compound is disclosed in U.S. Pat. No. 5,489,630 and is incorporated herein by reference in its entirety. The ratio of epoxide groups in the polyepoxide compound to active amine hydrogen atoms in polyetheramine is about 1.1:1 to 6:1.

Specific examples of polyetheramines are Jeffamine® M-600, Jeffamine® M-1000, Jeffamine® M-2005, Jeffamine® M-2070 amines, Jeffamine® D-2000, Jeffamine® ED-600, Jeffamine® ED-900, and Jeffamine® ED-2001 amines. The Jeffamine® materials are commercially available from the Huntsman Corp. The preferred polyetheramine is Jeffamine® M-1000 amine which is a monoamine terminated block copolymer of propylene oxide and ethylene oxide.

The reaction to produce the polyalkylene polyether modified polyepoxide resin is carried out by adding the polyetheramine to the polyepoxide resin component at a temperature range of 50 degrees C. to 120 degrees C. The addition is performed at a controlled rate to minimize the temperature increase created by the exothermic reaction.

(2) The Polyamine Component of the Curing Agent

In an embodiment, the polyamine component of the curing agent (2) is the reaction product of (2a) a polyethylene polyamine having 3 to 10 nitrogen atoms and (2b) a $C_1$ to $C_8$ aldehyde.

The polyethylene polyamine compounds having 3 to 10 nitrogen atoms (2a) that are useful in producing the curing agent polyamine component include a polyethylene polyamine according to formula (I):

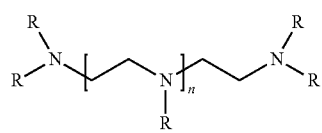

(I)

wherein R is independently a hydrogen atom or a group selected from $C_1$-$C_8$ linear, cyclic, and branched alkyl, alkenyl, and alkaryl groups; n is an integer from 1 to 8. Suitable examples of R include hydrogen atom, methyl, isopropyl, and benzyl group. Suitable polyethylene polyamine compounds having 3 to 10 nitrogen atoms according to the present disclosure include, but are not limited to, diethylenetriamine (DETA), triethylenetetramine (TETA), tetraethylenepentamine (TEPA), pentaethylenehexamine (PEHA), and mixtures thereof. Preferable examples of the polyethylene polyamine compounds having 3 to 10 nitrogen atoms include DETA, TETA, and TEPA, more preferably TETA and DETA, and most preferably DETA.

The polyethylene polyamine compounds having 3 to 10 nitrogen atoms can be used individually or mixed with one another. It is to be understood that commonly available polyethylene polyamine compounds having 3 to 10 nitrogen atoms such as TETA, TEPA, and PEHA are mixtures of linear and branched isomers and other congeners having cyclic structures. Some of the linear and branched isomers are shown above. These commonly available polyethylene polyamine compounds are included in the definition of polyethylene polyamine compounds of the present disclosure.

The polyethylene polyamine compounds having 3 to 10 nitrogen atoms can be substituted with alkyl groups. Examples include alkylated polyethylene polyamine as disclosed in U.S. Pat. No. 8,518,547 and benzylated polyethylene polyamine as disclosed in U.S. Pat. Nos. 8,147,964 and 8,168,296. The above referenced patents are hereby incorporated by reference.

The $C_1$ to $C_8$ aldehyde compounds (2b) that are useful in producing the curing agent polyamine component include but are not limited to, formaldehyde, acetaldehyde, propionaldehyde, butyraldehyde, isobutyraldehyde, trimethylacetaldehyde, 2-methylbutyraldehyde, isovaleraldehyde, valeraldehyde, hexanal, phenylacetaldehyde, benzaldehyde, vanillic aldehyde (also known as vanilline), o-tolualdehyde, o-anisaldehyde, salicylaldehyde, and 4-hydroxylbenzaldehyde. Preferable $C_1$ to $C_8$ aldehyde compounds include formaldehyde, acetaldehyde, benzaldehyde, tolualdehyde, o-anisaldehyde, and salicylaldehyde. More preferable $C_1$ to $C_8$ aldehyde compounds include formaldehyde, and benzaldehyde, and most preferable is formaldehyde. When formaldehyde is used as the $C_1$ to $C_8$ aldehyde compound, it is typically used as an aqueous solution with some methanol as stabilizer for easy handling. For easy handling, the trimer of formaldehyde, 1,3,5-trioxane, and the oligomer and polymer form, paraformaldehyde are used as equivalent to formaldehyde aqueous solution since both are solid. In the present disclosure, paraformaldehyde is used as equivalent to formaldehyde.

The polyethylene polyamine having 3 to 10 nitrogen atoms (2a) and the $C_1$ to $C_8$ aldehyde (2b) are reacted according to methods and conditions discussed below to form a reaction product which is the polyamine component (2) of the curing agent. In an embodiment, the reaction product of the polyethylene polyamine having 3 to 10 nitrogen atoms and the $C_1$ to $C_8$ aldehyde comprises at least one saturated heterocyclic compound having two nitrogen heteroatoms according to formula (II), below.

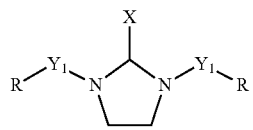

(II)

wherein X is independently selected from a hydrogen atom, a linear or branched $C_1$ to $C_4$ alkyl group and a substituted or un-substituted phenyl group, $Y_1$ is a direct bond or a divalent polyethylene polyamine group having 1 to 8 nitrogen atoms or a divalent polyethylene polyamine derivative having 1 to 8 nitrogen atoms, and R is independently a hydrogen atom or a group selected from $C_1$-$C_8$ linear, cyclic, and branched alkyl, alkenyl, and alkaryl groups. The $C_1$ to $C_4$ alkyl groups and the polyethylene polyamine groups having 1 to 8 nitrogen atoms may be branched or unbranched.

Preferable examples for X include hydrogen atom, methyl, ethyl, isopropyl, n-propyl, phenyl, iso-butyl, and n-butyl group. More preferable examples of X include hydrogen atom, methyl, and phenyl group. A most preferable example of X is hydrogen atom. Preferable examples of R include hydrogen atom, methyl, ethyl, isopropyl, n-propyl, iso-butyl, n-butyl, 3-methylbutyl, cyclohexyl, and benzyl group. More preferable examples of R include hydrogen atom, methyl, ethyl, isopropyl, iso-butyl, 3-methylbutyl, and benzyl group. The most preferable examples of R are hydrogen atom, methyl, isopropyl, and benzyl group.

In an embodiment of the present invention, the reaction product of the $C_1$ to $C_8$ aldehyde and the polyethylene polyamine having 3 to 10 nitrogen atoms includes at least one saturated heterocyclic compound having two nitrogen heteroatoms according to formula (II).

In another embodiment of the present invention, the reaction product of the $C_1$ to $C_8$ aldehyde and the polyethylene polyamine having 3 to 10 nitrogen atoms includes at least one saturated heterocyclic compound having two nitrogen heteroatoms according to formula (II) and at least one saturated fused bicyclic heterocyclic compound having two nitrogen heteroatoms according to formula (III):

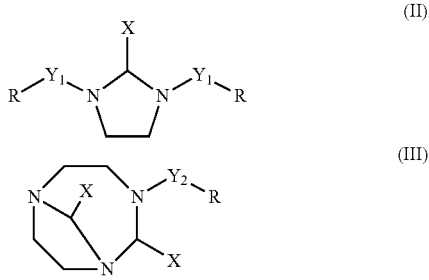

wherein X is independently selected from a hydrogen atom, a linear or branched $C_1$ to $C_4$ alkyl group and a substituted or un-substituted phenyl group, $Y_1$ is a direct bond or a divalent polyethylene polyamine group having 1 to 8 nitrogen atoms or a divalent polyethylene polyamine derivative having 1 to 8 nitrogen atoms, R is independently a hydrogen atom or a group selected from $C_1$-$C_8$ linear, cyclic, and branched alkyl, alkenyl, and alkaryl groups, and $Y_2$ is a direct bond or a divalent polyethylene polyamine group having 1 to 7 nitrogen atoms. The amine-epoxy curing agents can be used to cure, harden, and/or crosslink multifunctional epoxy resins. The $C_1$ to $C_4$ alkyl groups, the polyethylene polyamine groups having 1 to 8 nitrogen atoms, and the polyethylene polyamine groups having 1 to 7 nitrogen atoms may be branched or unbranched.

$Y_1$ and $Y_2$ are divalent polyethylene polyamine groups that include repeating units that may be linear or branched. Suitable repeating divalent polyethylene polyamine group units include the following formula (IV):

wherein R is independently a hydrogen atom or a group selected from $C_1$-$C_8$ linear, cyclic, and branched alkyl, alkenyl, and alkaryl groups, and R from two consecutive repeating units can form a 5- or 6-member ring with the backbone ethylene unit, and n=1 to 8 for $Y_1$ or n=1 to 7 for $Y_2$.

In a preferred embodiment, the polyethylene polyamine having 3 to 10 nitrogen atoms (2a) comprises DETA and the the $C_1$ to 08 aldehyde (2b) comprises formaldehyde. In this embodiment, the reaction product of DETA and formaldehyde, which is the polyamine component of the curing agent (2), comprises 1-(2-aminoethyl)imadazolidine. This corresponds to the case of general formula (II) wherein X is a hydrogen atom, Y1, in a first occurrence, is a divalent polyethylene polyamine group having 1 nitrogen, and in a second occurrence is a hydrogen atom, and where R is a hydrogen atom in both occurrences. It also corresponds to the case of general formula (IV) wherein R is a hydrogen atom and n is 1, for $Y_1$ in its first occurrence.

The polyamine component can comprise at least one multifunctional amine. Multifunctional amine, as used herein, describes compounds with amine functionality and which contain two (2) or more active amine hydrogens.

Non-limiting examples of multifunctional amines that are within the scope of the present invention include, but are not limited to, an aliphatic amine, a cycloaliphatic amine, an aromatic amine, a Mannich base derivative of an aliphatic amine, a cycloaliphatic amine, or an aromatic amine, a polyamide derivative of an aliphatic amine, a cycloaliphatic amine, or an aromatic amine, an amidoamine derivative of an aliphatic amine, a cycloaliphatic amine, or an aromatic amine, an amine adduct derivative of an aliphatic amine, a cycloaliphatic amine, or an aromatic amine, and the like, or any combination thereof.

More than one multifunctional amine can be used in the compositions of the present invention. For example, the at least one multifunctional amine can comprise an aliphatic amine and a Mannich base derivative of a cycloaliphatic amine. Also, the at least one multifunctional amine can comprise one aliphatic amine and one different aliphatic amine.

Exemplary aliphatic amines include polyethyleneamines (ethylene diamine (EDA), diethylene triamine (DETA), triethylenetetraamine (TETA), tetraethylenepentamine (TEPA), and the like), polypropyleneamines, aminopropylated ethylenediamines, aminopropylated propylenediamines, 1,6-hexanediamine, 3,3,5-trimethyl-1,6-hexanediamine, 3,5,5-trimethyl-1,6-hexanediamine, 2-methyl-1,5-pentanediamine (commercially available as Dytek-A), and the like, or combinations thereof. Additionally, the poly (alkylene oxide) diamines and triamines commercially available under the Jeffamine name from Huntsman Corporation, are useful in the present invention. Illustrative examples include, but are not limited to, Jeffamine® D-230, Jeffamine® D-400, Jeffamine® D-2000, Jeffamine® D-4000, Jeffamine® T-403, Jeffamine® EDR-148, Jeffamine® EDR-192, Jeffamine® C-346, Jeffamine® ED-600, Jeffamine® ED-900, Jeffamine® ED-2001, and the like, or combinations thereof.

Cycloaliphatic and aromatic amines include, but are not limited to, 1,2-diaminocyclohexane, 1,3-diaminocyclohexane, 1,4-diaminocyclohexane, hydrogenated ortho-toluenediamine, hydrogenated meta-toluenediamine, metaxylylene diamine, hydrogenated metaxylylene diamine (referred to commercially as 1,3-BAC), isophorone diamine (IPDA), various isomers or norbornane diamine, 3,3'-dimethyl-4,4'-diaminodicyclohexyl methane, 4,4'-diaminodicyclohexyl methane, 2,4'-diaminodicyclohexyl methane, a mixture of methylene bridged poly(cyclohexyl-aromatic) amines, and the like, or combinations thereof. The mixture of methylene bridged poly(cyclohexyl-aromatic)amines is abbreviated as either MBPCAA or MPCA, and is described in U.S. Pat. No. 5,280,091, which is incorporated herein by reference in its entirety. In one aspect of the present invention, the at least one multifunctional amine is a mixture of methylene bridged poly(cyclohexyl-aromatic)amines (MPCA).

Mannich base derivatives can be made by the reaction of the above described aliphatic amines, cycloaliphatic amines, or aromatic amines with phenol or a substituted phenol and formaldehyde. An exemplary substituted phenol used to make Mannich bases with utility in the present invention is cardanol, which is obtained from cashew nut shell liquid. Alternatively, Mannich bases can be prepared by an exchange reaction of a multifunctional amine with a tertiary amine containing a Mannich base, such as tris-dimethylaminomethylphenol (commercially available as Ancamine® K54 from Air Products and Chemicals, Inc.) or bis-dimethylaminomethylphenol.

Polyamide derivatives can be prepared by the reaction of an aliphatic amine, cycloaliphatic amine, or aromatic amine with dimer fatty acid, or mixtures of a dimer fatty acid and a fatty acid. Amidoamine derivatives can be prepared by the reaction of an aliphatic amine, cycloaliphatic amine, or aromatic amine with fatty acids.

Amine adducts can be prepared by the reaction of an aliphatic amine, cycloaliphatic amine, or aromatic amine with an epoxy resin, for example, with the diglycidyl ether of bisphenol-A, the diglycidyl ether of bisphenol-F, or epoxy novolac resins. The aliphatic, cycloaliphatic, and aromatic amines also can be adducted with monofunctional epoxy resins, such as phenyl glycidyl ether, cresyl glycidyl ether, butyl glycidyl ether, other alkyl glycidyl ethers, and the like.

In another aspect of the present disclosure, the curing agent includes a co-curing agent. The co-curing agent may be an amidoamine curing agent, an aliphatic curing agent, a polyamide curing agent, a cycloaliphatic curing agent, or a Mannich base curing agent which also includes phenalkamine.

Method of Making the Curing Agent Composition

In an embodiment, the curing agent comprises the reaction product of: (1) a polyalkylene polyether modified polyepoxide resin component, and (2) a polyamine component, which is the reaction product of (2a) a polyethylene polyamine having 3 to 10 nitrogen atoms and (2b) a $C_1$ to $C_8$ aldehyde. A preliminary step in making the curing agent composition is producing the polyamine component (2) by reacting the polyethylene polyamine compounds (2a) with the aldehyde (2b). The reaction of the $C_1$ to $C_8$ aldehyde and the polyethylene polyamine compounds having 3 to 10 nitrogen atoms may proceed at a reaction temperature of about −20° C. to about 150° C., about 0° C. to about 120° C., about 0° C. to about 100° C., about 0° C. to about 90° C., about 0° C. to about 80° C., about 20° C. to about 100° C., about 20° C. to about 90° C., about 20° C. to about 80° C., about 20° C. to about 70° C. The reaction of the $C_1$ to $C_8$ aldehyde and the polyethylene polyamine compounds is exothermic, thus, cooling might be necessary to maintain reaction temperature at desired range.

Water is formed from the reaction of the aldehyde and the polyethylene polyamine compounds, and is typically removed under designated temperature and pressure. Water from the reaction may be removed at different temperature and pressure than the condition when the reaction of the aldehyde and the polyethylene polyamine compounds takes place. The water formed may be removed by direct atmosphere distillation or vacuum distillation, or removed by forming azeotropic mixture with a solvent. Azeotropic solvent with water includes, but is not limited to, toluene, xylene, acetonitrile, n-butanol, isobutanol, and t-butanol, heptane, and hexane. Suitable azeotropic solvents include toluene, xylene, acetonitrile, and n-butanol.

The reaction of the $C_1$ to $C_8$ aldehyde and the polyethylene polyamine compounds having 3 to 10 nitrogen atoms to form the amine-epoxy curing agent of the present disclosure may be conducted in a solvent media. Suitable solvent for the reaction includes but is not limited to, water, acetonitrile, alcohol such as methanol, ethanol, n-propanol, isopropanol, n-butanol, Dowanol PM, t-butanol, isobutanol, and benzyl alcohol, and hydrocarbons such as toluene, xylene, hexane, and heptane. Suitable reaction solvent includes water, methanol, ethanol, n-propanol, isopropanol, n-butanol, Dowanol PM and benzyl alcohol. The solvent may be removed after the reaction is complete, or remain as part of the curing agent. For example, benzyl alcohol may remain as plasticizer for the curing agent.

The maximum mole ratio of the $C_1$ to $C_8$ aldehyde to the polyethylene polyamine compounds having 3 to 10 nitrogen atoms is half of the number of amine hydrogen, to 1, mathematically expressed below:

$$\left(\frac{\text{number of amine hydrogen}}{2}\right):1$$

The mole ratio of the $C_1$ to $C_8$ aldehyde to the polyethylene polyamine compounds having 3 to 10 nitrogen atoms is at least about 90%, or about 80%, or about 75%, or about 70%, or about 65%, or about 60%, or about 55%, or about 50%, or about 45%, or about 40%, or about 30%, or about 25%, or about 20%, or about 10% of the maximum mole ratio of the C1 to C8 aldehyde to the polyethylene polyamine compounds having 3 to 10 nitrogen atom to 1.

The reaction to prepare the curing agent comprising the reaction product of: (1) a polyalkylene polyether modified polyepoxide resin component, and (2) a polyamine component, which is the reaction product of (2a) a polyethylene polyamine having 3 to 10 nitrogen atoms and (2b) a $C_1$ to $C_8$ aldehyde is conducted by charging the polyamine component (2) to a reaction vessel, and adding the polyalkylene polyether modified polyepoxide resin component (1) at a controlled rate.

A curing agent comprising the reaction product of: (1) a polyalkylene polyether modified polyepoxide resin component, and (2) a polyamine component, which is the reaction product of (2a) a polyethylene polyamine having 3 to 10 nitrogen atoms and (2b) a $C_1$ to $C_8$ aldehyde can be produced with various reactant ratios. It is within the scope of the present invention for the stoichiometric ratio of the equivalent number of the active amine hydrogens of the polyamine component (2) to the equivalent number of epoxy groups in the polyalkylene polyether modified polyepoxide resin component (1) to range from about 50:1 to about 2:1. In another aspect, the ratio is about 40:1 to about 2:1, about 30:1 to about 2:1, about 25:1 to about 2:1, about 20:1 to about 2:1, about 15:1 to about 2:1, about 10:1 to about 2:1, about 8:1 to about 2:1, about 6:1 to about 2:1, about 5:1 to about 2:1, about 4:1 to about 2:1, or about 3:1 to about 2:1.

In accordance with the present invention, a method of making a curing agent composition is provided. This method comprises adding the polyalkylene polyether modified polyepoxide resin component (1) to the polyamine component (2) at a controlled rate over a time period generally from about 1 hour to about 4 hours. After the addition step, the reaction can be allowed to continue for approximately another 30 minutes to about 2 hours to provide for a substantially complete reaction. The reaction can be done in a reactor, vessel, or other container. The reaction may proceed at a reaction temperature of about 20° C. to about 160° C., about 20° C. to about 150° C., about 50° C. to about 150° C., or about 50° C. to about 140° C. The temperature ranges during the addition step and the following step to complete the reaction need not to be identical, and can be different. Non-limiting examples of the synthesis of curing agent compositions in accordance with the present invention are illustrated in the examples.

In preparing the reaction product, the curing agent composition can become very viscous, and in such cases, a solvent can be added to the reactor. Exemplary solvents include, but are not limited to, n-butanol, toluene, xylene, and the like, Dowanol™ solvents, or mixtures thereof. The solvent can be removed via distillation after the reaction is complete, and optionally replaced with water to keep the viscosity low or to form an aqueous curing agent composition.

In one aspect of the invention, before the reaction product cools, at least one multifunctional amine having 2 or more active amine hydrogens can be added to lower the viscosity and to target a desired AHEW for the curing agent composition. Optionally, water is added to reach a desired percent solids content for such aqueous curing agent composition.

In an embodiment, the curing agent comprises (i) the reaction product of: (1) a polyalkylene polyether modified polyepoxide resin component, and (2) a polyamine component; and (ii) water.

In another embodiment, the curing agent comprises (i) the reaction product of: (1) a polyalkylene polyether modified polyepoxide resin component, and (2) a polyamine component; and (ii) at least one multifunctional amine having 2 or more active amine hydrogens.

In another embodiment, the curing agent comprises (i) the reaction product of: (1) a polyalkylene polyether modified polyepoxide resin component, and (2) a polyamine component; (ii) at least one multifunctional amine having 2 or more active amine hydrogens; and (iii) water.

In another embodiment of the present invention, the curing agent includes a co-curing agent. The co-curing agent may be an amidoamine curing agent, an aliphatic curing agent, a polyamide curing agent, a cycloaliphatic curing agent, or a Mannich base curing agent which also includes phenalkamine. Generally, the curing agent compositions have an amine hydrogen equivalent weight (AHEW) based on 100% solids from about 30 to about 500. Further, such curing agent compositions can have an AHEW based on 100% solids in the range from about 50 to about 450, from about 50 to about 400, from about 50 to about 350, from about 50 to about 300, from about 50 to about 250, from about 50 to about 200, from about 100 to about 250, or from about 100 to about 200.

Amine-Epoxy Compositions

Generally, amine-epoxy coating compositions include a curing agent and at least one multifunctional epoxy resin. An amine-epoxy composition, in accordance with the present disclosure, includes, in a first component, the curing agent as described above; and, in a second component, an epoxy composition comprising at least one multifunctional epoxy resin having at least two epoxide groups per molecule. The at least one multifunctional epoxy resin having at least two epoxide groups per molecule can be a liquid epoxy resin, a solid epoxy resin, mixture of liquid and solid epoxy resin, and can be used as neat without solvent, or as an aqueous epoxy emulsion, or an aqueous solid epoxy dispersion. The curing agent in accordance with the present disclosure can be used to cure, harden, and/or crosslink the epoxy resin.

Multifunctional epoxy resins are well known to those of skill in the art. One class of epoxy resins suitable for use in the present invention comprises the glycidyl ethers of polyhydric phenols, including the glycidyl ethers of dihydric phenols. Illustrative examples include, but are not limited to, the glycidyl ethers of resorcinol, hydroquinone, bis-(4-hydroxy-3,5-difluorophenyl)-methane, 1,1-bis-(4-hydroxyphenyl)-ethane, 2,2-bis-(4-hydroxy-3-methylphenyl)-propane, 2,2-bis-(4-hydroxy-3,5-dichlorophenyl) propane, 2,2-bis-(4-hydroxyphenyl)-propane (commercially known as bisphenol A), bis-(4-hydroxyphenyl)-methane (commercially known as bisphenol F, and which may contain varying amounts of 2-hydroxyphenyl isomers), and the like, or any combination thereof. Additionally, advanced dihydric phenols of the following structure also are useful in the present invention:

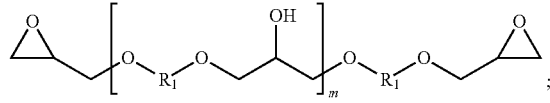

where m is an integer, and $R_1$ is a divalent hydrocarbon radical of a dihydric phenol, such as those dihydric phenols listed above. Materials according to this formula can be prepared by polymerizing mixtures of a dihydric phenol and epichlorohydrin, or by advancing a mixture of a diglycidyl ether of dihydric phenol. While in any given molecule the value of m is an integer, the materials are invariably mixtures which can be characterized by an average value of m, which is not necessarily a whole number. Polymeric materials with an average value of m between 0 and about 7 can be used in one aspect of the present disclosure.

In another aspect, epoxy novolac resins, which are the glycidyl ethers of novolac resins, can be used as multifunctional epoxy resins in accordance with the present disclosure. In yet another aspect, the at least one multifunctional epoxy resin is a diglycidyl ether of bisphenol-A (DGEBA), an advanced or higher molecular weight version of DGEBA, a diglycidyl ether of bisphenol-F, an epoxy novolac resin, or any combination thereof. Higher molecular weight versions or derivatives of DGEBA are prepared by the advancement process, where excess DGEBA is reacted with bisphenol-A to yield epoxy terminated products. The epoxy equivalent weights (EEW) for such products range from about 450 to 3000 or more. Because these products are solid at room temperature, they are often referred to as solid epoxy resins.

DGEBA or advanced DGEBA resins are often used in coating formulations due to a combination of their low cost and generally high performance properties. Commercial grades of DGEBA having an EEW ranging from about 174 to about 250, and more commonly from about 185 to about 195, are readily available. At these low molecular weights, the epoxy resins are liquids and are often referred to as liquid epoxy resins. It is understood by those skilled in the art that most grades of liquid epoxy resin are slightly polymeric, since pure DGEBA has an EEW of 174. Resins with EEW's between 250 and 450, also generally prepared by the advancement process, are referred to as semi-solid epoxy resins because they are a mixture of solid and liquid at room temperature. Generally, multifunctional resins with EEW's based on solids of about 160 to about 750 are useful in the prevent invention. In another aspect the multifunctional epoxy resin has an EEW in a range from about 170 to about 250.

The relative amount chosen for the epoxy composition versus that of the curing agent composition, can vary depending upon, for example, the end-use article, its desired properties, and the fabrication method and conditions used to produce the end-use article. For instance, in coating applications using certain amine-epoxy compositions, incorporating more epoxy resin relative to the amount of the curing agent composition, can result in coatings which have increased drying time, but with increased hardness and improved appearance as measured by gloss. Amine-epoxy compositions of the present invention generally have stoichiometric ratios of epoxy groups in the epoxy composition to amine hydrogens in the curing agent composition ranging from about 1.5:1 to about 0.7:1. For example, such amine-epoxy compositions can have stoichiometric ratios of epoxy to amine hydrogen from about 1.5:1 to about 0.7:1, or about 1.4:1 to about 0.7:1, or about 1.3:1 to about 0.7:1, or about 1.2:1 to about 0.7:1, or about 1.1:1 to about 0.7:1, or about 1.0:1 to about 0.7:1, or about 0.9:1 to about 0.7:1, or about 1.2:1 to about 0.8:1, or about 1.1:1 to about 0.9:1.

Optionally, other additives may be present in the amine-epoxy composition. If desired, either one or both of the amine curing agent and curable epoxy resin composition may be mixed, before curing, with one or more customary additives, for example, a stabilizer, extender, filler, reinforcing agent, pigment, dyestuff, plasticizer, tackifier, rubber, accelerator, diluent or any mixture thereof. Other customary additives can include, but are not limited to, solvents (including water), accelerators, plasticizers, fillers, fibers such as glass or carbon fibers, pigments, pigment dispersing agents, rheology modifiers, and thixotropes.

Compositions in accordance with the present invention can comprise at least one multifunctional amine. Multifunctional amine, as used herein, describes compounds with amine functionality and which contain two (2) or more active amine hydrogens.

Articles

The present invention also is directed to articles of manufacture comprising the compositions disclosed herein. For example, an article can comprise an amine-epoxy composition which comprises the reaction product of a curing agent composition and an epoxy composition. Articles of manufacture produced from amine-epoxy compositions disclosed herein include, but are not limited to, adhesives, coatings, primers, sealants, curing compounds, construction products, flooring products, and composite products. Further, such coatings, primers, sealants, or curing compounds can be applied to metal or cementitious substrates. Coatings based on these amine-epoxy compositions can be solvent-free or can contain diluents, such as water or organic solvents, as needed for the particular application. Coatings can contain various types and levels of pigments for use in paint and primer applications. Amine-epoxy coating compositions comprise a layer having a thickness ranging from 40 to 400 µm (micrometer), preferably 80 to 300 µm, more preferably 100 to 250 µm, for use in a protective coating applied on to metal substrates. In addition, for use in a flooring product or a construction product, coating compositions comprise a layer having a thickness ranging from 50 to 10,000 µm, depending on the type of product and the required end-properties.

Numerous substrates suitable for the application of coatings of the present invention include, but are not limited to, concrete and various types of metals and alloys, such as steel and aluminum. Coatings of the present invention are suitable for the painting or coating of large metal objects or cementitious substrates including ships, bridges, industrial plants and equipment, and floors.

Coatings of this invention can be applied by any number of techniques including spray, brush, roller, paint mitt, and the like. In order to apply very high solids content or 100% solids coatings of the present disclosure, plural component spray application equipment can be used, in which the amine and epoxy components are mixed in the lines leading to the spray gun, in the spray gun itself, or by mixing the two components together as they leave the spray gun. Using this technique can alleviate limitations with regard to the pot life of the formulation, which typically decreases as both the amine reactivity and the solids content increases. Heated plural component equipment can be employed to reduce the viscosity of the components, thereby improving ease of application.

Construction and flooring applications include compositions comprising the amine-epoxy compositions of the present invention in combination with cement, concrete or other materials commonly used in the construction industry. Applications of compositions of the present invention include, but are not limited to use of the composition as a primer, a deep penetrating primer, a coating, a curing compound, and/or a sealant for new or old concrete. As a primer or a sealant, the amine-epoxy compositions of the present disclosure can be applied to surfaces to improve adhesive bonding prior to the application of a coating. Crack injection and crack filling products also can be prepared from the compositions disclosed herein. Amine-epoxy compositions of the present invention can be mixed with cementitious materials such as cement or concrete mix to form epoxy modified cements, tile grouts, and the like.

The epoxy modified cement composition may be used for coating, adhesive, sealer, grouting and mortar. Particularly, it is suitable for a mortar or coating, more particularly used for self-leveling floor coating.

The epoxy modified cement composition, according to the present invention, includes a combination of (A) an epoxy composition comprising at least one multifunctional epoxy resin having at least two epoxide groups per molecule, (B) a curing agent comprising water and the reaction product of: (1) a polyalkylene polyether modified polyepoxide resin component, and (2) a polyamine component, which is the reaction product of (2a) a polyethylene polyamine having 3 to 10 nitrogen atoms and (2b) a $C_1$ to $C_8$ aldehyde, and (C) a solid component comprising at least one hydraulic inorganic binder. The hydraulic inorganic binder can be cement.

The epoxy modified cement composition includes a curing agent of the present invention in a sufficient concentration and in a ratio such that a cured epoxy modified cement solid article formed from the epoxy modified cement composition has a compressive strength greater than about 6,000 psi as measured by ASTM C-539. The compressive strength in one embodiment is measured at 7 days after application of the epoxy modified cement composition. In another embodiment, the compressive strength is measured 28 days after the application of the epoxy modified cement composition.

The invention is further illustrated by the following examples, which are not to be construed as imposing limitations to the scope of this invention. Various other aspects, embodiments, modifications, and equivalents thereof which, after reading the description herein, may suggest themselves to one of ordinary skill in the art without departing from the spirit of the present invention or the scope of the appended claims.

EXAMPLES

The following synthesis examples are provided to illustrate certain aspects or embodiments of the instant invention and shall not limit the scope of the claims appended hereto.

Synthesis Examples

Diethylenetriamine (DETA) and formaldehyde aqueous solution were purchased from Aldrich. The reaction product was analyzed by gas chromatography (GC) to determine the amount of unreacted DETA, Metrohm titrator using Karl Fisher titration method for residual water content, Brookfield viscometer for viscosity, Metrohm titrator for amine value, and nuclear magnetic resonance (NMR) for chemical composition. The NMR experiments were performed at ambient temperature employing the Bruker DRX-400 FT-NMR spectrometer equipped with a 10 mm BBO probe. Quantitative $^{13}$C NMR data was acquired using inverse-gated decoupling, a 45° pulse, and a 6 second relaxation delay. The samples were dissolved in chloroform-d with chromium acetylacetonate added as a relaxation agent. The chemical shift scale was referenced to the solvent peak. GC analysis was performed on Agilent 7890 Gas Chromatograph equipped with a Agilent CP-Volamine 0.32 mm×30 m—column and a Flame Ionization Detector. The samples were prepared as 1% solutions in isopropanol then placed in 2 mL autosampler vials for GC analysis. Standard solutions ranging from 0.005 to 0.51 wt % DETA in isopropanol were used to create a six point external, linear calibration curve to quantify the residual DETA in the samples. The square of correlation coefficient ($R^2$) value for the calibration curves are 0.999.

Example 1. Synthesis of Polyamine 1 (PA1): Reaction Product of DETA with Formaldehyde at Molar Ratio of 1.60:1 Formaldehyde to DETA DETA (650 g) was charged to a reactor equipped with a nitrogen inlet, a condenser, an addition funnel, and an overhead stirrer. To DETA was added formaldehyde aqueous solution (818.1 g) via an addition funnel to maintain a temperature below 60° C. After the addition, the reaction was kept at 60° C. for 30 minutes. Water was then removed under reduced pressure. The product was obtained as a clear liquid in quantitative yield with an amine value of 857 meqKOH/g, viscosity of 9,470 mPa·s at 25° C., water content of 0.41%, and residual DETA of 1.3%. NMR analysis showed that 39 mol % of DETA formed 1-(2-aminoethyl) imidazolidine, which corresponds to 37 wt % to the total weight in the product by calculation.

Example 2. Synthesis of Polyalkylene Polyether Modified Polyepoxide Resin A Via Polyalkylene Polyether Polyol Polyethylene glycol 1000 (379 g) and 490 g of a bisphenol-A diglycidyl ether having an epoxy equivalent weight of 190 were charged to a stirred reactor equipped with a thermocouple and a reflux condenser. A catalyst, BF$_3$-amine complex, commercially available from Air Products and Chemicals, Inc., as Anchor® 1040 (3 g) was added to the reactor. While the reactor contents were stirred, the reactor temperature was increased to 140° C. This temperature was maintained until the epoxy equivalent weight increased to about 475 to 500. The reactor contents were then cooled, resulting in a reaction product designated as Resin A. The epoxy equivalent weight of Resin A was 480 and the viscosity at 40° C. was 33 Poise (3.3 Pa·s).

Example 3. Synthesis of Polyalkylene Polyether Modified Polyepoxide Resin B Via Polyalkylene Polyether Polyol Example 3 utilized the same process as described in Example 2. The reactants were 3043.8 g of polyethylene glycol 2000 and 1144.6 g of a bisphenol-A diglycidyl ether having an epoxy equivalent weight of 190. After following the process of Example 2, the final product was designated as Resin B. The epoxy equivalent weight of Resin B was 1392 and the viscosity at 70° C. was 668 mPa·s. Viscosity was determined using a Brookfield DV-II+ cone and plate viscometer, CP52 spindle, 100 rpm. Using Gel Permeation Chromatography (GPC), THF solvent, and polystyrene calibration standards, the $M_n$ (number-average molecular weight) was 4017, and the $M_w$ (weight average molecular weight) was 7866. Low molecular weight unreacted epoxy resin was excluded from molecular weight distribution and from the determination of $M_n$ and $M_w$.

Example 4. Synthesis of Polyalkylene Polyether Modified Polyepoxide Resin C Via Poly(Alkylene Oxide) Mono-Amine A reactor was equipped with a nitrogen inlet, a condenser, an addition funnel, and an overhead stirrer. Epoxy resin Epon 828 (250 g) was charged to the reactor. The content was heated up to 80° C. Jeffamine M1000 amine (available from the Huntsman Corp., AHEW of 489 mgKOH/eq) (214.5 g) was melted at 70° C. oven and charged to an addition funnel. Jeffamine M1000 was then charged to the Epon 828 resin in the reactor over about 30 minutes to keep temperature below 95° C. The temperature was raised to 95° C. and held at that temperature for 1 hour. The product Resin C was obtained as a clear liquid and has a viscosity of 8,650 cPs, and an EEW of 409.

Example 5. Synthesis of Polyalkylene Polyether Modified Polyepoxide Resin D Via Poly(Alkylene Oxide) Mono-Amine Example 5 utilized the same process as described in Example 4. The reactants were Jeffamine 2070 (available from the Huntsman Corp., AHEW of 1040 mgKOH/eq) (273.7 g) and Epon 828 (150 g). The product Resin D was obtained as clear liquid and has an EEW of 578.

Example 6. Synthesis of Curing Agent 1 (CA1) from Polyamine PA1 of Example 1 and Resin A of Example 2

Polyamine PA1 of example 1 (169.4 g) was charged to a reactor equipped with a nitrogen inlet, a condenser, an addition funnel, and an overhead stirrer. The content was heated up to 80° C. Resin A of example 2 (127.1 g) was warmed up to 80° C. and added to an addition funnel. Resin A was charged to a reactor over about 40 minutes to keep temperature below 95° C. The temperature was raised to 95° C. and held at that temperature for 1 hour. Water (198 g) was then added to the reaction under vigorous stirring. The product curing agent 1 (CA1) was obtained as a clear liquid at 60% solid and has a viscosity of 3,850 cPs, and an amine value of 315 mg KOH/g, and a calculated AHEW of 222.

Example 7. Synthesis of Curing Agent 2 (CA2) from Polyamine PA1 of Example 1 and Resin C of Example 4

Example 7 utilized the same process as described in Example 6. The reactants were polyamine PA1 of example 1 (166.7 g), Resin C of example 4 (125 g) and water (194 g). The product curing agent 2 (CA2) was obtained as a clear liquid and at 60% solid has an amine value of 320 mgKOH/g, and a calculated AHEW of 226.

Example 8. Synthesis of Curing Agent 3 (CA3) from Polyamine PA1 of Example 1 and Isophorone Diamine with Resin A of Example 2

Example 8 utilized the same process as described in Example 6. The reactants were polyamine PA1 of example 1 (60.3 g), isophorone diamine (obtained from Aldrich, 112 g), Resin A of example 2 (241.2 g) and water (338.4 g). The product curing agent 3 (CA3) was obtained as a clear liquid and at 55% solid and has a viscosity of 8,590 cPs, and an amine value of 169 mgKOH/g, and a calculated AHEW of 249.

Example 9. Synthesis of Curing Agent 4 (CA4) from Polyamine PA1 of Example 1 and Isophorone Diamine with Resin C of Example 4

Example 9 utilized the same process as described in Example 6. The reactants were polyamine PA1 of example 1 (56.6 g), isophorone diamine (obtained from Aldrich, 105 g), Resin C of example 4 (226 g) and water (194 g). The product curing agent 4 (CA4) was obtained as a clear liquid and at 55% solid and has a viscosity of 5,250 cPs, an amine value of 177 mgKOH/g, and a calculated AHEW of 257.

Example 10. Synthesis of Curing Agent 5 (CA5) from Polyamine PA1 of Example 1 and Isophorone Diamine with Resin A of Example 2

Example 10 utilized the same process as described in Example 6. The reactants were isophorone diamine (obtained from Aldrich, 94.5 g), Resin A of example 2 (165.4 g) and water (260 g). The product curing agent 5 (CA5) was obtained as a clear liquid and at 50% solid and has a viscosity of 39,230 cPs, an amine value of 121 mgKOH/g, and a calculated AHEW of 277.

Example 11. Synthesis of Curing Agent 6 (CA6) from Polyamine PA1 of Example 1 and Isophorone Diamine with Resin A of Example 2

Example 11 utilized the same process as described in Example 6. The reactants were polyamine PA1 of example 1 (87.7 g), isophorone diamine (obtained from Aldrich, 95.2 g), Resin A of example 2 (232.5 g) and water (339 g). The product curing agent 6 (CA6) was obtained as clear liquid and at 55% solid and has a viscosity of 30,650 cPs, and an amine value of 175 mgKOH/g, and a calculated AHEW of 248.

Example 12. Synthesis of Curing Agent 7 (CA7) from Polyamine PA1 of Example 1 and Isophorone Diamine with Resin C of Example 4

Example 12 utilized the same process as described in Example 6. The reactants were polyamine PA1 of example 1 (83.2 g), isophorone diamine (obtained from Aldrich, 90 g), Resin C of example 4 (219.8 g) and water (324 g). The product curing agent 7 (CA7) was obtained as a clear liquid and at 55% solid and has a viscosity of 3,637 cPs, and an amine value of 197 mgKOH/g, and a calculated AHEW of 255.

Example 13. Synthesis of Curing Agent 8 (CA8) from Polyamine PA1 of Example 1 and Isophorone Diamine with Resin A of Example 2

Example 13 utilized the same process as described in Example 6. The reactants were polyamine PA1 of example 1 (14.8 g), isophorone diamine (obtained from Aldrich, 130.5 g), Resin A of example 2 (240.2 g) and water (383 g). The product curing agent 8 (CA8) was obtained as a clear liquid and at 50% solid and has a viscosity of 21,320 cPs, and an amine value of 131 mgKOH/g, and a calculated AHEW of 276.

Example 14. Synthesis of Curing Agent 9 (CA9) from Polyamine PA1 of Example 1 and Isophorone Diamine with Resin C of Example 4

Example 14 utilized the same process as described in Example 6. The reactants were polyamine PA1 of example 1 (13.9 g), isophorone diamine (obtained from Aldrich, 125.4 g), Resin C of example 4 (229.6 g) and water (368 g). The product curing agent 9 (CA9) was obtained as a clear liquid and at 50% solid and has a viscosity of 12,820 cPs, and an amine value of 136 mgKOH/g, and a calculated AHEW of 285.

Example 15. Synthesis of Curing Agent 10 (CA10) from Polyamine PA1 of Example 1 and Isophorone Diamine with Resin a of Example 2

Example 15 utilized the same process as described in Example 6. The reactants were polyamine PA1 of example 1 (30 g), isophorone diamine (obtained from Aldrich, 120 g), Resin A of example 2 (237.2 g) and water (388 g). The product curing agent 10 (CA10) was obtained as a clear liquid and at 50% solid and has a viscosity of 14,900 cPs, and an amine value of 135 mgKOH/g, and a calculated AHEW of 276.

Example 16. Synthesis of Curing Agent 11 (CA11) from Polyamine PA1 of Example 1 and Isophorone Diamine with Resin C of Example 4

Example 16 utilized the same process as described in Example 6. The reactants were polyamine PA1 of example 1 (28.8 g), isophorone diamine (obtained from Aldrich, 115.4 g), Resin C of example 4 (223.12 g) and water (368 g). The product curing agent 11 (CA11) was obtained as a clear liquid and at 50% solid and has a viscosity of 7,390 cPs, and an amine value of 147 mgKOH/g, and a calculated AHEW of 285.

Testing of Curing Agents

Epon 828 (EEW 190) liquid epoxy resin, solid resin dispersions Ancarez AR555 (obtained from Evonik Corporation, 55% solid, EEW 550), and Epodil 748 (obtained from Evonik Corporation, EEW 290) were used for the test. The test methods are outlined in Table 1. Anquamine 721 (A721) is a waterborne curing agent based on alkylated aliphatic amine-epoxy adduct, and has a viscosity of 40,000 cPs. Anquamine 401 (A401) is a waterborne curing agent based on aliphatic amine-epoxy adduct and has a viscosity of 30,000 cPs at 70% solid. Both are available from Evonik Corporation.

TABLE 1

General Test Methods

| Property | Measurements | ASTM METHOD |
|---|---|---|
| Drying time (hours) | BK recorder Thin film set times<br>Phase 1: set to touch<br>Phase 2: tack free<br>Phase 3: dry hard | D5895 |
| Coating Appearance | Gloss (20°)/gloss (60°) | D523 |
| Solvent Resistance | MEK Double Rubs | D7835/D7835M |
| Hardness | Persoz Pendulum Hardness (s)<br>Shore D | D4366<br>D2240 |

Test Examples of Curing Agents

Test Example 1. The Thin Film Set Time (TFST) of Coatings Using Liquid Epoxy Resin Epon 828, and Resin Dispersion AR555

The thin film set time was determined using a Beck-Koller recorder, in accordance with ASTM D5895. The amine-epoxy coatings were prepared on standard glass panels at a wet film thickness of about 150 micron WFT (wet film thickness) using a Bird applicator. The coatings were cured at 23° C./50% relative humidity (RH), and 10. ° C./60% relative humidity (RH). The data are summarized in Table 2. The curing agent of the present invention has low viscosity and the coatings containing the curing agent of the present invention shows much faster thin film set time at 23° C. and 10° C.

TABLE 2

Thin film set time using CA1 with liquid epoxy resin

| Curing agents | CA1 | A721 | A401 | CA1 | CA1 |
|---|---|---|---|---|---|
| Solid % | 60% | 50% | 70% | 60% | 60% |
| phr | 120 | 160 | 70 | 140 | 36 |
| Resin | Epon 828 | Epon 828 | Epon 828 | Epon 828 | AR555 |
| Thin film set time (h) | 23° C. | 23° C. | 23° C. | 10° C. | 10° C. |
| Stage 1 | 0.9 | 2 | 2.3 | 0.8 | 0.5 |
| Stage 2 | 1.3 | 3.5 | 3.4 | 1.3 | 0.8 |
| Stage 3 | 2.4 | 5.5 | 5.1 | 5.3 | 3.8 |

Test Example 2: Solvent Resistance Test

The clear epoxy-amine coating compositions using the present invention was tested for MEK double rub. The MEK double rub test is an indicator of how well the through cure properties of the film have developed. The higher the number of MEK double rubs, then the grater the film integrity. The coating made from CA1 and Ancarez AR555 was applied on cold-rolled steel substrate at 150 microns wet film thickness, and cured at 23° C. and 50% RH for 5 days. The coating easily passed >200 MEK double rub test.

Test Example 3: Coating Properties of Clear Coats Using the Curing Agents of the Present Invention The curing agents and epoxy resin were mixed at the phr described in Table 3, and further diluted with water to a mix viscosity of about 200 cPs. Clear coatings were applied onto glass substrate at 150 microns wet film thickness and cured at 23° C. and 50% RH. The coatings were evaluated for Persoz hardness at 1 day (d1) and 7 day (d7) and gloss during potlife. Also viscosity build during potlife and drying times were determined. The data are summarized in Table 3 and clearly show that the curing agents of the present invention provide coatings with fast dry time and hardness development with both liquid epoxy resin and solid epoxy resion dispersion.

TABLE 3

Coating properties of clear coats

| | | Curing agent | | | | |
|---|---|---|---|---|---|---|
| | | CA1 | CA1 | CA3 | CA4 | CA6 |
| resin | | Epon 828 | AR555 | AR555 | AR555 | AR555 |
| phr | | 140 | 38 | 34 | 35 | 34 |
| solid % | | 45% | 50% | 44% | 46% | 42% |
| Viscosity (cPs) | 0" | 160 | 180 | 220 | 220 | 210 |
| | 10" | 220 | 210 | 160 | 160 | 150 |
| | 20" | 290 | 240 | 120 | 120 | 110 |
| | 30" | 650 | 320 | 120 | 120 | 90 |
| | 40" | 2500 | 460 | 100 | 100 | 80 |
| | 50" | | 880 | 80 | 80 | 70 |
| | 60" | | | 70 | 70 | 90 |
| | 70" | | | 60 | 60 | 60 |
| | 80" | | | 50 | 50 | 50 |
| | 90" | | | 80 | 80 | 60 |

| | | 20° | 60° | 20° | 60° | 20° | 60° | 20° | 60° | 20° | 60° |
|---|---|---|---|---|---|---|---|---|---|---|---|
| Specular gloss (GU) | 10" | 48 | 73 | 135 | 127 | 159 | 137 | 159 | 137 | 132 | 130 |
| | 20" | 45 | 71 | 136 | 127 | 167 | 140 | 167 | 140 | 156 | 136 |
| | 30" | 29 | 56 | 134 | 128 | 166 | 139 | 166 | 139 | 166 | 140 |
| | 40" | 23 | 48 | 135 | 128 | 153 | 134 | 153 | 134 | 157 | 136 |
| | 50" | | | 92 | 115 | 149 | 133 | 149 | 133 | 154 | 135 |
| | 60" | | | | | 148 | 133 | 148 | 133 | 149 | 133 |

TABLE 3-continued

Coating properties of clear coats

|  |  |  |  |  |  | 137 | 128 | 137 | 128 | 153 | 134 |
|---|---|---|---|---|---|---|---|---|---|---|---|
|  | 70" |  |  |  |  | 137 | 128 | 137 | 128 | 153 | 134 |
|  | 80" |  |  |  |  | 125 | 122 | 125 | 122 | 143 | 131 |
|  | 90" |  |  |  |  | 132 | 126 | 132 | 126 | 132 | 127 |

|  |  | d1 | d7 | d1 | d7 | d1 | d7 | d1 | d7 | d1 | d7 |
|---|---|---|---|---|---|---|---|---|---|---|---|
| Persoz | 10" | 243 | 291 | 200 | 278 | 173 | 307 | 173 | 307 | 161 | 287 |
| hardness | 20" | 255 | 283 | 199 | 290 | 199 | 316 | 199 | 316 | 173 | 293 |
| (s) | 30" | 236 | 280 | 211 | 288 | 214 | 324 | 214 | 324 | 189 | 311 |
|  | 40" | 256 | 291 | 217 | 300 | 228 | 334 | 228 | 334 | 205 | 312 |
|  | 50" |  |  | 195 | 276 | 235 | 336 | 235 | 336 | 211 | 320 |
|  | 60" |  |  |  |  | 247 | 339 | 247 | 339 | 222 | 324 |
|  | 70" |  |  |  |  | 250 | 344 | 250 | 344 | 230 | 330 |
|  | 80" |  |  |  |  | 252 | 341 | 252 | 341 | 231 | 334 |
|  | 90" |  |  |  |  | 259 | 344 | 259 | 344 | 231 | 328 |
| Thin film | ph1 | 0.40 |  | 0.40 |  | 0.5 |  | 0.5 |  | 0.4 |  |
| set time | ph2 | 0.60 |  | 0.80 |  | 0.8 |  | 0.8 |  | 0.6 |  |
| (h) | ph3 | 0.80 |  | 1.40 |  | 1 |  | 1 |  | 1 |  |

Curing agent

|  |  | CA7 |  | CA8 |  | CA9 |  | CA10 |  | CA11 |  |
|---|---|---|---|---|---|---|---|---|---|---|---|
| resin |  | AR555 |  | AR555 |  | AR555 |  | AR555 |  | AR555 |  |
| phr |  | 35 |  | 38 |  | 39 |  | 38 |  | 39 |  |
| solid % |  | 49% |  | 45% |  | 45% |  | 45% |  | 45% |  |
| Viscosity | 0" | 210 |  | 220 |  | 220 |  | 210 |  | 210 |  |
| (cPs) | 10" | 150 |  | 120 |  | 120 |  | 120 |  | 120 |  |
|  | 20" | 110 |  | 100 |  | 100 |  | 100 |  | 100 |  |
|  | 30" | 90 |  | 90 |  | 90 |  | 80 |  | 80 |  |
|  | 40" | 80 |  | 100 |  | 100 |  | 70 |  | 70 |  |
|  | 50" | 70 |  | 100 |  | 100 |  | 50 |  | 50 |  |
|  | 60" | 90 |  | 80 |  | 80 |  | 80 |  | 80 |  |
|  | 70" | 60 |  | 90 |  | 90 |  | 70 |  | 70 |  |
|  | 80" | 50 |  | 80 |  | 80 |  | 60 |  | 60 |  |
|  | 90" | 60 |  | 70 |  | 70 |  | 80 |  | 80 |  |

|  |  | 20° | 60° | 20° | 60° | 20° | 60° | 20° | 60° | 20° | 60° |
|---|---|---|---|---|---|---|---|---|---|---|---|
| Specular | 10" | 132 | 130 | 169 | 140 | 169 | 140 | 168 | 139 | 168 | 139 |
| gloss | 20" | 156 | 136 | 168 | 139 | 168 | 139 | 159 | 136 | 159 | 136 |
| (GU) | 30" | 166 | 140 | 166 | 138 | 166 | 138 | 164 | 138 | 164 | 138 |
|  | 40" | 157 | 136 | 153 | 134 | 153 | 134 | 162 | 137 | 162 | 137 |
|  | 50" | 154 | 135 | 156 | 135 | 156 | 135 | 156 | 135 | 156 | 135 |
|  | 60" | 149 | 133 | 138 | 129 | 138 | 129 | 137 | 129 | 137 | 129 |
|  | 70" | 153 | 134 | 139 | 129 | 139 | 129 | 128 | 125 | 128 | 125 |
|  | 80" | 143 | 131 | 139 | 129 | 139 | 129 | 138 | 129 | 138 | 129 |
|  | 90" | 132 | 127 | 126 | 123 | 126 | 123 | 131 | 125 | 131 | 125 |

|  |  | d1 | d7 | d1 | d7 | d1 | d7 | d1 | d7 | d1 | d7 |
|---|---|---|---|---|---|---|---|---|---|---|---|
| Persoz | 10" | 161 | 287 | 162 | 292 | 162 | 292 | 169 | 303 | 169 | 303 |
| hardness | 20" | 173 | 293 | 189 | 308 | 189 | 308 | 194 | 315 | 194 | 315 |
| (s) | 30" | 189 | 311 | 192 | 319 | 192 | 319 | 209 | 318 | 209 | 318 |
|  | 40" | 205 | 312 | 209 | 329 | 209 | 329 | 215 | 326 | 215 | 326 |
|  | 50" | 211 | 320 | 217 | 330 | 217 | 330 | 208 | 331 | 208 | 331 |
|  | 60" | 222 | 324 | 228 | 290 | 228 | 290 | 232 | 333 | 232 | 333 |
|  | 70" | 230 | 330 | 237 | 337 | 237 | 337 | 238 | 301 | 238 | 301 |
|  | 80" | 231 | 334 | 231 | 332 | 231 | 332 | 243 | 311 | 243 | 311 |
|  | 90" | 231 | 328 | 236 | 338 | 236 | 338 | 248 | 329 | 248 | 329 |
| Thin film | ph1 | 0.4 |  | 0.3 |  | 0.3 |  | 0.5 |  | 0.5 |  |
| set time | ph2 | 0.6 |  | 0.5 |  | 0.5 |  | 0.8 |  | 0.8 |  |
| (h) | ph3 | 1 |  | 0.8 |  | 0.8 |  | 1 |  | 1 |  |

Test Example 4: Test of Adhesion to Dry and Wet Concrete Using the Curing Agents of Present Invention in Primer Formulations B25 (based on DIN 1045) concrete blocks were used for the test. Prior to conducting any test, the concrete blocks were prepared for by removing any loose concrete with a wire brush followed by vacuum cleaning to remove any dust. For dry concrete adhesion test, they were conditioned at 10° C./60% RH in order to attain the testing temperature prior to the primer application.

For wet concrete adhesion test, the concrete blocks were placed in a container with water on supports making sure the water level was approximately 1 cm below the tile surface and water was able to circulate underneath the blocks. Excess water was removed from the surface before the primer application.

Prior to primer application, the surface temperature of the concrete blocks was determined using infrared thermometer and the moisture content of the concrete was determined using Testo 606-1 hygrometer, preset material 3 (concrete). For dry concrete adhesion test, the surface temperature is about 10° C. for both wet and dry concrete and moisture content of 2% for dry test, and 3.4% for wet test.

The primer composition was specified in Table 4 and Table 5, and further diluted with water to a mix viscosity of about 200 cPs. The primer was applied onto the concrete blocks by brush at application thickness of 400 g/m². After application, the drying process was followed by thumb twist drying time until the primer was dry hard. The primer was then left to cure for 7 days before measuring the pull off adhesion.

Before the adhesion testing, a trench was drilled through the coating and the coating surface was lightly sanded. Dollies were glued onto the dust free coating surface using Loctite 3425 epoxy glue obtained from Manutan. 6 Dollies were tested for each primer sample. The glue was left to cure for 1 day and dollies were pulled off using a PAT-adhesion tester. Both the tensile stress at break and the type of failure were recorded, and summarized in Table 4 and Table 5. The data clearly demonstrate that the curing agents of the present invention provide coatings with fast dry time at low temperature on wet and dry concrete, and good adhesion to concrete.

TABLE 4

Performance properties of primers on dry concrete at low temperature (10° C./ 60% RH) at coating thickness of 400 g/m²

| | Curing agent | | | | | | | |
|---|---|---|---|---|---|---|---|---|
| | CA1 | CA1 | blend of CA1/CA5 33%/67% wt | blend of CA1/CA5 33%/67% wt | CA3 | CA4 | CA9 | CA10 |
| resin | AR555 | Epon 828/ Epodil 748 90/10 | Epon 828/ Epodil 748 90/10 | AR555 | AR555 | AR555 | AR555 | AR555 |
| phr | 30 | 143 | 132 | 47 | 34 | 35 | 39 | 38 |
| solid % | 56% | 71% | 73% | 47% | 44% | 46% | 45% | 45% |
| Thumb twist drying time[1] | 6 | 6 | 9-10 | 3.5 | 2.3 | 3.8 | 4.5 | 2 |
| Tensile stress to break[2] | 7.1 | 8.5 | 9 | 7.4 | 6.5 | 6.3 | 7.5 | 7.4 |
| Type of failure[3] | 100% A | 100% A | 100% A | 97% A; 3% AB | 72% A; 28% AB | 93% A; 7% AB | 76% A; 24% AB | 100% A |

[1]Coating on B25 concrete block, stages rated according to ASTM D 1640
[2]Determined using PAT adhesion tester, ISO 4624
[3]A = cohesive failure of substrate; A/B = adhesive failure between substrate and first coat;

TABLE 5

Performance properties of primers on wet concrete at low temperature (10° C./ 60% RH) at coating thickness of 400 g/m²

| | Curing agent | | | | | | |
|---|---|---|---|---|---|---|---|
| | CA1 | blend of CA1/CA5 33%/67% wt | blend of CA1/CA5 33%/67% wt | CA3 | CA4 | CA9 | CA10 |
| resin | Epon 828/ Epodil 748 90/10 | Epon 828/ Epodil 748 90/10 | AR555 | AR555 | AR555 | AR555 | AR555 |
| phr | 143 | 132 | 47 | 34 | 35 | 39 | 38 |
| solid % | 71% | 73% | 47% | 44% | 46% | 45% | 45% |
| Thumb twist drying time[1] | 8-24 | 8-24 | 4.5 | 2.3 | 2 | 3.8 | 4.5 |
| Tensile stress to break[2] | 5.8 | 6.5 | 4.7 | 6.5 | 6.3 | 7.5 | 7.4 |
| Type of failure[3] | 95% A; 5% AB | 98% A; 2% AB | 98% A; 2% AB | 97% A; 3% AB | 72% A; 28% AB | 93% A; 7% AB | 76% A; 24% AB |

[1]Coating on B25 concrete block, stages rated according to ASTM D 1640
[2]Determined using PAT adhesion tester, ISO 4624
[3]A = cohesive failure of substrate; A/B = adhesive failure between substrate and first coat;

Test Example 5: Evaluation of White Paint Formulations Using the Curing Agents of the Present Invention White paint formulations were prepared according to the amounts specified in Table 6. Part A was prepared first. Components 1a to 3 were mixed at low shear until homogeneous, then components 4 and 5 were added and mixed at low shear until homogeneous, followed by grinding at high speed. Component 6 was added to adjust viscosity. Part B was added to Part A and mixed mechanically for 1-2 minutes until homogeneous.

Coatings based on above paint formulations were applied at 225 microns wet film thickness glass panels through potlife and basic performance parameters were determined after 1 day (d1) and 7 days (d7). Mix viscosity was determined in time to determine the potlife of the paint formulations. Also thin film set time was determined and Persoz hardness and gloss were followed during potlife. The data are summarized in Table 7.

Paint flocculation was tested by filling a 100 mL bottle with 50 mL of de-mineralized water and adding 5 drops of the white paint formulation. The bottle was then shaken and put upside down to assess if any particles were present on the bottle walls.

The data in Table 7 clearly demonstrate that the white paint formulations using the curing agent of the present invention are very stable and provide semi-glossy white paint with fast dry time, and hardness development.

TABLE 6

White paint formulations

| | | | White paint 1 | White paint 2 |
|---|---|---|---|---|
| A | 1a | CA5 | 12.17 | 10.14 |
| | 1b | CA1 | 3.08 | 4.96 |
| | 2 | Zetasperse 3800 | 0.54 | 0.55 |
| | 3 | Surfynol DF-62 | 0.05 | 0.05 |
| | 4 | Kronos 2160 (TiO2) | 12.63 | 12.87 |
| | 5 | Tafigel PUR 55 (thickner) | 0.32 | 0.32 |
| | 6 | Water | 9.9 | 10.11 |
| B | 7 | Epon 828 | 10.2 | 10.4 |
| | 8 | Epodil 748 | 1.1 | 1.1 |

TABLE 7

White paint formulation data summary

| | | White Paint 1 | | White Paint 2 | |
|---|---|---|---|---|---|
| Additional water (g) | | 7 | | 6 | |
| Mix viscosity (cPs)[1] | 0" | 230 | | 240 | |
| | 15" | 170 | | 250 | |
| | 30" | 190 | | 220 | |
| | 60" | 180 | | 240 | |
| | 90" | 210 | | 250 | |
| | 120" | 210 | | 300 | |
| | 150" | 260 | | 320 | |
| | | 20° | 60° | 20° | 60° |
| Specular gloss (GU) | 15" | 78 | 95 | 53 | 88 |
| | 30" | 80 | 96 | 58 | 90 |
| | 60" | 87 | 96 | 64 | 92 |
| | 90" | 86 | 96 | 62 | 90 |
| | 120" | 85 | 95 | 50 | 84 |
| | 150" | 82 | 94 | 36 | 77 |
| | | d 1 | d 7 | d 1 | d 7 |
| Persoz hardness (s) | 15" | 97 | 242 | 119 | 249 |
| | 30" | 114 | 240 | 127 | 249 |
| | 60" | 145 | 277 | 154 | 274 |
| | 90" | 168 | 288 | 176 | 271 |
| | 120" | 176 | 268 | 183 | 273 |
| | 150" | 183 | 283 | 195 | 274 |
| Thin film set time (h) | ph 1 | 1.3 | | 0.8 | |
| | ph 2 | 3 | | 1.8 | |
| | ph 3 | 4 | | 2.5 | |
| Flocculation test | | pass | | pass | |

Test Example 6: Cement Stability of the Amine-Epoxy Compositions Using the Curing Agents of the Present Invention Table 8 summarizes the amine-epoxy compositions using the curing agents of the present invention at 10% solids. Cement stability testing was conducted by mixing the amine-based curing agent, epoxy resin, and water to achieve 10% solids, as indicated in Table 8. To this diluted amine-epoxy composition at 10% solids, 1 g of Portland cement was added and mixed thoroughly. Many commercially available amine-epoxy emulsions do not remain stable upon addition of the cement and the increase in alkalinity, and tend to curdle. Table 8 shows that each of the amine-epoxy compositions, exhibited a stable emulsion after addition of the cement.

TABLE 8

Cement stability test

| | CA1 | CA2 | CA3 | CA4 | CA6 | CA7 | CA8 | CA9 | CA10 | CA11 |
|---|---|---|---|---|---|---|---|---|---|---|
| curing agent (g) | 3.43 | 3.48 | 3.81 | 3.88 | 3.80 | 3.87 | 4.21 | 4.29 | 4.21 | 4.29 |
| Epon 828 resin (g) | 2.94 | 2.91 | 2.91 | 2.87 | 2.91 | 2.87 | 2.90 | 2.86 | 2.90 | 2.86 |
| Water (g) | 43.63 | 43.61 | 43.29 | 43.25 | 43.29 | 43.26 | 42.90 | 42.86 | 42.90 | 42.86 |
| Cement stability | stable | stable | stable | stable | stable | stable | stable | stable | stable | stable |

Test Example 7: Epoxy Modified Cement Compositions Using the Curing Agents of the Present Invention The composition of epoxy modified cement is shown in Table 9, and Table 10 illustrates the composition of Part A. The components in Part A were emulsified to achieve a stable emulsion. Part B was premixed at least 24 hours prior to compounding, then Part A was added. Part C was premixed before adding to the Part A and Part B mixture. Working time, flowability, compressive strength, and shore D hardness were tested.

For comparison, a commercially available urethane modified cement system FasTop 12 S-Urethnane Slurry System from Sherwin Williams was prepared, and the composition is shown in Table 11. Part A and Part B were mixed with low speed drill, then Part C was added and mixed until homogeneous.

Shore D samples were prepared in a 6"×9"×½" mold. The compressive strength was determined according to ASTM C-579 with a cylinder of 1 inch diameter by 1 inch height. The samples were cured at 23° C. and 50% RH. The flowability and working time tests were conducted by filling the samples into a circular mold with a dimension of 3 inches diameter and 1¼ inches height. After releasing the mold, the flowability was recorded as the diameter of the sample at specified times, and the working time was determined as the time when the sample stops flowing back and leaves a distinct line in the sample by slicing the sample with a metal spatula outward from center toward the edge of the sample.

The test data is summarized in Table 12. The epoxy modified cement composition offers long working time, good smooth surface appearance and excellent compressive strength.

TABLE 9

Composition of epoxy modified cement

| | | |
|---|---|---|
| Binder % | | 5.5% |
| water:cement ratio | | 0.37 |
| Filler:Binder | | 16.1:1 |
| Part A | Epon 828/Epodil 748 emulsion | 5.65 |
| Part B | CA1 | 3.1 |
| | Airase 4500 | 0.05 |
| | Water | 8.05 |
| Part C | White Portland Cement | 31 |
| | Berkely #1 dry (from US Silica) | 51.1 |
| | Melflux 2651 | 0.16 |
| | Calcium sulfoaluminate | 0.66 |
| Total | | 100 |

TABLE 10

Composition of Part A: Epon 828/Epodil 748 emulsion

| | |
|---|---|
| Epon 828 | 50.4 |
| Triton X405 | 2.5 |
| Epodil 748 | 11.1 |
| DI Water | 36 |
| Total | 100 |

TABLE 11

Composition of polyurethane modified cement

| | | |
|---|---|---|
| Part A | FasTop 12S-Urethane Slurry GP4080 | 11.4% |
| Part B | FasTop 12S-Urethane Slurry GP4080 Hardener | 11.4% |
| Part C | GP508CLC-50 5080 Light Gray | 77.2% |

TABLE 12

Test data summary of epoxy modified cement and urethane modified cement

| Properties | Patent example: Epoxy modified cement | Comparison example: urethane modified cement |
|---|---|---|
| Working time (minutes) | 76 | 8 |
| Flowability at 30 seconds (inches) | 8.00 | 7.250 |
| Flowability at 1 minute (inches) | 8.25 | 7.375 |
| Flowability at 5 minutes (inches) | 8.50 | 7.750 |
| Flowability at 10 minutes (inches) | 8.50 | 8.000 |
| Flowability at 30 minuntes (inches) | 8.50 | 8.125 |
| Compressive strength at 7 days (psi) | 6,942 | 4,757 |
| Compressive strength at 28 days (psi) | 8,164 | 4,706 |
| Shore D Hardness | | |
| 1 day | 75 | 76 |
| 4 day | 82 | 75 |
| 7 day | 82 | 78 |
| Surface evaluation | Smooth, no bubbles/pinholes | Many bubbles/pinholes |

The invention claimed is:

1. A curing agent composition comprising the reaction product of:
   (a) a polyamine comprising at least one saturated heterocyclic compound having two nitrogen heteroatoms according to formula (II)

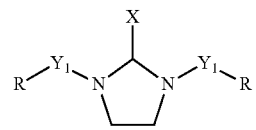

(II)

wherein X is selected from a hydrogen atom, a linear or branched $C_1$ to $C_4$ alkyl group and a substituted or unsubstituted phenyl group, $Y_1$ is a direct bond or a divalent polyethylene polyamine group having 1 to 8 nitrogen atoms, and R is independently a hydrogen atom or a group selected from $C_1$-$C_8$ linear, cyclic, and branched alkyl, alkenyl, and alkaryl groups; and
   (b) a polyalkylene polyether modified polyepoxide resin.

2. The curing agent composition of claim 1 further comprises at least one multifunctional amine having 2 or more active amine hydrogens.

3. The curing agent composition of claim 2 further comprises water.

4. The curing agent composition of claim 2, wherein the at least one multifunctional amine is an aliphatic amine, a cycloaliphatic amine, an aromatic amine, a Mannich base derivative of an aliphatic amine, a cycloaliphatic amine, or an aromatic amine, a polyamide derivative of an aliphatic amine, a cycloaliphatic amine, or an aromatic amine, an amidoamine derivative of an aliphatic amine, a cycloaliphatic amine, or an aromatic amine, an amine adduct derivative of an aliphatic amine, a cycloaliphatic amine, or an aromatic amine, or any combination thereof.

5. The curing agent composition of claim 1, wherein X is hydrogen and R is hydrogen.

6. The curing agent composition of claim 1, wherein the polyalkylene polyether modified polyepoxide resin comprises the reaction product of: a polyalkylene polyether polyol and a polyepoxide compound.

7. The curing agent composition of claim 6 wherein the polyalkylene polyether polyol comprises polyethylene glycol.

8. The curing agent composition of claim 1, wherein the polyalkylene polyether modified polyepoxide resin comprises the reaction product of: a polyepoxide compound and a polyetheramine.

9. The curing agent composition of claim 1, further comprises water.

10. The curing agent composition of claim 1, further comprises isophorone diamine.

11. The curing agent composition of claim 1, further comprises a co-curing agent selected from an amidoamine curing agent, an aliphatic curing agent, a polyamide curing agent, a cycloaliphatic curing agent, or a Mannich base curing agent.

12. An amine-epoxy composition comprising:
the reaction product of a curing agent and an epoxy composition, wherein the epoxy composition comprises at least one multifunctional epoxy resin, and wherein the curing agent comprises:
a reaction product of at least one polyamine and at least one polyalkylene polyether modified polyepoxide resin, wherein the at least one polyamine comprises at least one saturated heterocyclic compound having two nitrogen heteroatoms according to formula (II)

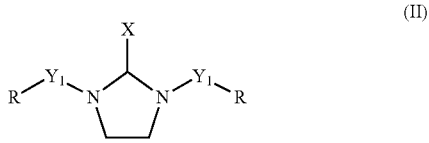

(II)

wherein X is selected from a hydrogen atom, a linear or branched $C_1$ to $C_4$ alkyl group and a substituted or unsubstituted phenyl group $Y_1$ is a direct bond or a divalent polyethylene polyamine group having 1 to 8 nitrogen atoms, and R is independently a hydrogen atom or a group selected from $C_1$-$C_8$ linear, cyclic, and branched alkyl, alkenyl and alkaryl groups.

13. The composition of claim 12, wherein the composition further comprises water.

14. An article of manufacture comprising the composition of claim 12.

15. The article of claim 14, wherein the article is an adhesive, a coating, a primer, a sealant, a curing compound, a construction product, a flooring product, or a composite product.

16. A process for the preparation of a curing agent for aqueous epoxy resin compositions, comprising:
(a) reacting a polyethylene polyamine having 3 to 10 nitrogen atoms with at least one aldehyde having 1 to 8 carbon atoms to produce a polyethylene polyamine component, wherein the polyethylene polyamine component comprises at least one saturated heterocyclic compound having two nitrogen heteroatoms according to formula (II)

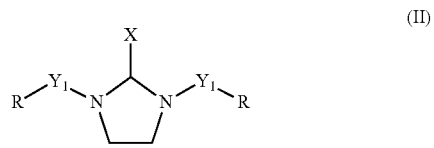

(II)

wherein X is selected from a hydrogen atom, a linear or branched $C_1$ to $C_4$ alkyl group and a substituted or unsubstituted phenyl group, $Y_1$ is a direct bond or a divalent polyethylene polyamine group having 1 to 8 nitrogen atoms, and R is independently a hydrogen atom or a group selected from $C_1$-$C_8$ linear, cyclic, and branched alkyl, alkenyl, and alkaryl group; and
(b) reacting the polyethylene polyamine component with at least one polyalkylene polyether modified polyepoxide resin to produce a curing agent.

17. The process of claim 16, further comprising
(c) mixing the curing agent with water.

18. An epoxy modified cement composition comprising:
(A) an epoxy composition comprising at least one multifunctional epoxy resin having at least two epoxide groups per molecule;
(B) a curing agent comprising water and the reaction product of: (1) a polyalkylene polyether modified polyepoxide resin component, and (2) a polyamine component comprising at least one saturated heterocyclic compound having two nitrogen heteroatoms according to formula (II)

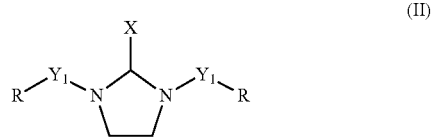

(II)

wherein X is selected from a hydrogen atom, a linear or branched $C_1$ to $C_4$ alkyl group and a substituted or unsubstituted phenyl group, $Y_1$ is a direct bond or a divalent polyethylene polyamine group having 1 to 8 nitrogen atoms, and R is independently a hydrogen atom or a group selected from $C_1$-$C_8$ linear, cyclic, and branched alkyl alkenyl, and alkaryl groups; and
(C) a solid component comprising at least one hydraulic inorganic binder.

* * * * *

UNITED STATES PATENT AND TRADEMARK OFFICE
CERTIFICATE OF CORRECTION

| | |
|---|---|
| PATENT NO. | : 10,465,039 B2 |
| APPLICATION NO. | : 15/596996 |
| DATED | : November 5, 2019 |
| INVENTOR(S) | : Shiying Zheng et al. |

It is certified that error appears in the above-identified patent and that said Letters Patent is hereby corrected as shown below:

On the Title Page

Please delete the Related U.S. Application Data in items (63) and (60).

Signed and Sealed this
Twenty-third Day of February, 2021

Drew Hirshfeld
*Performing the Functions and Duties of the*
*Under Secretary of Commerce for Intellectual Property and*
*Director of the United States Patent and Trademark Office*